United States Patent [19]

Schauss

[11] Patent Number: 5,746,204

[45] Date of Patent: May 5, 1998

[54] DISEASE INDICATOR ANALYSIS SYSTEM

[75] Inventor: Mark A. Schauss, Incline Village, Nev.

[73] Assignee: Carbon Based Corporation, Incline Village, Nev.

[21] Appl. No.: 568,752

[22] Filed: Dec. 7, 1995

[51] Int. Cl.$^6$ ............................................. A61B 5/00
[52] U.S. Cl. ................................................. 128/630
[58] Field of Search ............................ 128/630, 920, 128/923, 924

[56] References Cited

U.S. PATENT DOCUMENTS

| | | |
|---|---|---|
| 4,290,114 | 9/1981 | Sinay . |
| 4,731,725 | 3/1988 | Suto et al. . |
| 4,733,354 | 3/1988 | Potter et al. . |
| 5,023,785 | 6/1991 | Adrion et al. . |
| 5,437,278 | 8/1995 | Wilk . |
| 5,551,436 | 9/1996 | Yago ............................. 128/670 |

OTHER PUBLICATIONS

Blood Test Evaluation Copyright 1988 by Life Balances, Inc. (2 pages).

*Primary Examiner*—Jennifer Bahr
*Assistant Examiner*—Samuel Gilbert
*Attorney, Agent, or Firm*—Robert O. Guillot

[57] ABSTRACT

The present invention is a computerized medical diagnostic method. It includes a first database containing a correlation of a plurality of diseases with a plurality of indicators associated with each such disease. A second database includes human experience test results associated with each indicator. An individual's test results are then compared with the second database data to determine presence levels for each indicator. Thereafter the presence levels are compared with the data in the first database to provide a determination of diseases associated with the various indicator presence levels.

10 Claims, 1 Drawing Sheet

DISEASE INDICATOR ANALYSIS SYSTEM

BACKGROUND OF THE INVENTION

1. Field of the Invention

The present invention relates generally to automated medical diagnosis systems, and more particularly to such systems which compare patient diagnostic data with predetermined ranges of specific indicators to provide a specific disease diagnosis.

2. Description of the Prior Art

Medical research in the second half of the 20th century has produced, and continues to produce, an ever increasing body of knowledge. The complexity and interrelationships of various diseases and the indicators that may be detected in various diagnostic tests for the diseases are more than sufficient to tax the capacity of most medical practitioners. To aid medical practitioners in disease diagnosis, computerized expert systems have been, and are being developed to collate medical diagnostic data with various diseases to guide physicians in prescribing treatments for their patients. Such prior art medical diagnostic systems do not adequately provide an analytical framework for analyzing the individual patient's diagnostic results to collate such results into a disease indicator pattern.

SUMMARY OF THE INVENTION

The present invention is a computerized medical diagnostic method. It includes a first database containing a correlation of a plurality of diseases with a plurality of indicators associated with each such disease. A second database includes human experience test results associated with each indicator. An individual's test results are then compared with the second database data to determine presence levels for each indicator. Thereafter the presence levels are compared with the data in the first database to provide a determination of diseases associated with the various indicator presence levels.

It is an advantage of the present invention that it provides a method for automated analysis of an individual's test results to provide increased accuracy in disease identification.

It is another advantage of the present invention that it provides increased accuracy in automated disease identification systems by determining indicator presence levels for use in the disease identification analysis.

It is a further advantage of the present invention that it provides an automated medical diagnostic database system wherein indicator test results for specific individuals are automatically categorized as increased, normal or decreased for increased accuracy in disease determination.

These and other features and advantages of the present invention will become well understood upon reading the following detailed description of the invention.

IN THE DRAWINGS

FIG. 1 is a block diagram of the analytical method of the present invention.

DETAILED DESCRIPTION OF THE PREFERRED EMBODIMENTS

Figure 1:
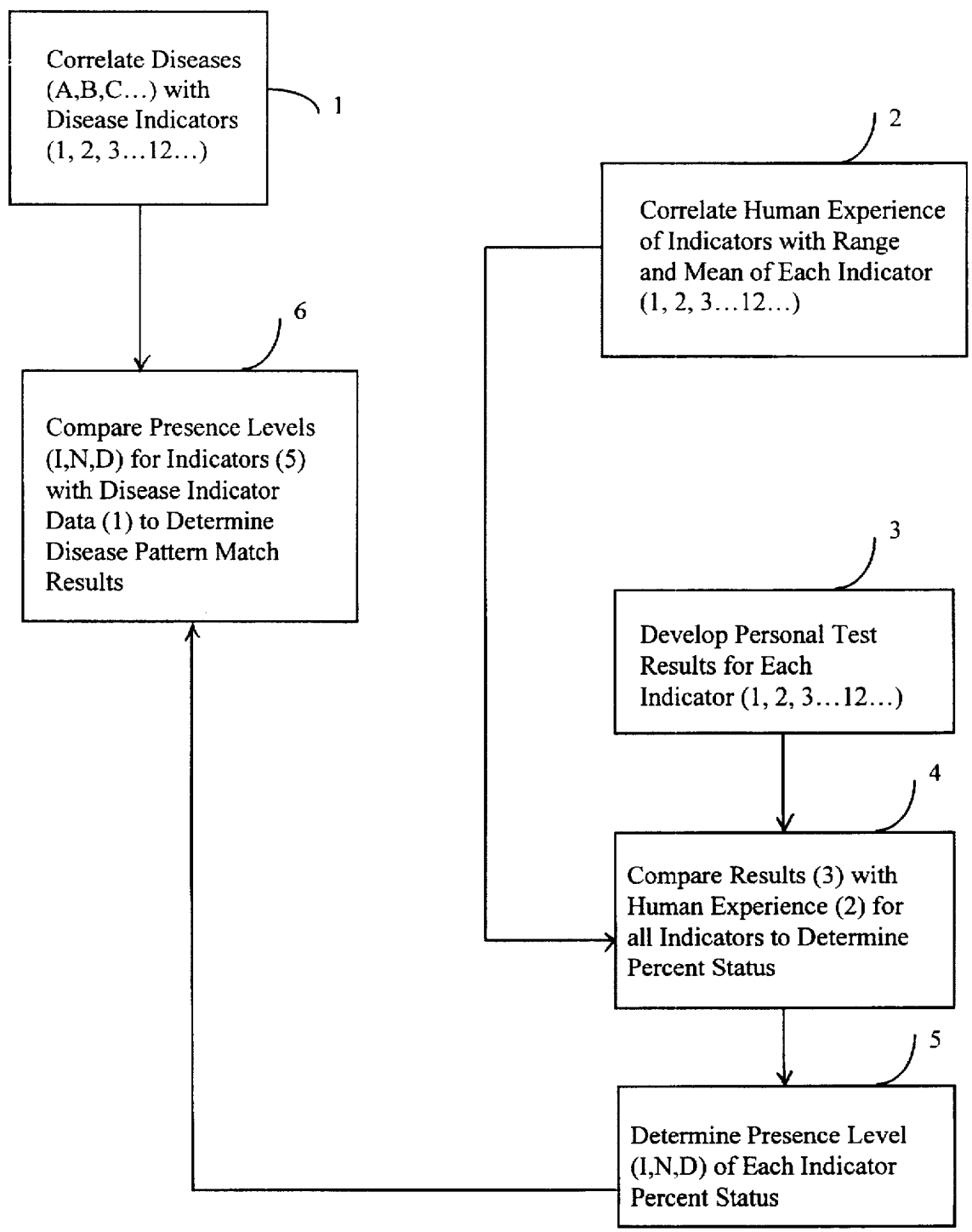

Generally, the system of the present invention involves the comparison of test results, typically from blood or other bodily fluids of an individual with known indicators for various diseases to determine the probability that an individual might have particular ones of the diseases. The method is basically accomplished in six steps which are depicted in FIG. 1 and described herebelow.

FIG. 1 is a schematic diagram setting forth the various steps in the analytical method of the present invention. As depicted therein, step 1 is the creation of a database for utilization within a computer diagnostic system. The database a correlation of various diseases, denoted generally as A, B, C . . . , with levels (Increased, Normal, Decreased) of various specific indicators, denoted generally as 1, 2, 3 . . . 12 . . . , in a computerized database.

Table 1 depicts the step 1 database relationship of various diseases (denoted A, B, C . . . with known indicators for the particular disease (denoted 1, 2, 3 . . . 12). It is seen that various ones of the indicators in increased (I), normal (N) or decreased (D) levels are associated with various ones of the diseases.

TABLE 1

| DISEASE (A, B, C, . . .) | INDICATORS (1, 2, 3, 4, 5, 6, 7, 8, 9, 10, 11, 12, . . .) |
|---|---|
| A | 1I, 2D, 7D, 9I, 10I |
| B | 1D, 3D, 6D, 8D, 10I, 12I |
| C | 2I, 3D, 5D, 7I, 10D |
| . | . |
| . | . |

By way of specific example, Table 2 describes three specific diseases, acute myocardial infarction, acquired hemolytic anemia and acromegaly, with related indicators. There are, of course, many diseases and several significant indicators for each, and medical research daily discovers, new diseases and derives new indicators for particular diseases. Thus, step 1 actually comprises a tabulation of known medical research of diseases and the indicator levels indicative of those diseases.

TABLE 2

ACUTE MYOCARDIAL INFARCTION

Indicators

Increased levels: Alkaline Phosphatase, Cholesterol, Creatinine, GGT, LDH, WBC, Neutrophils, Triglycerides, BUN, Uric Acid
Normal levels: Total Bilirubin, Calcium
Decreased levels: albumin, Iron, Sodium

ACQUIRED HEMOLYTIC ANEMIA (AUTOIMMUNE)

Indicators

Increased levels: SGOT, SGPT, Basophils, Total Bilirubin, Creatinine, LDH, Monocytes, Phosphorus, BUN, Uric Acid
Normal levels: none
Decreased levels: Hematocrit, Hemoglobin

ACROMEGALY

Indicators

Increased levels: Alkaline Phosphatase, Calcium, Creatinine, Glucose, Phosphorous, Potassium, Sodium, BUN
Normal levels: none
Decreased levels: none As depicted in FIG. 1, step 2 of the method of the present invention is the creation of a second database which comprises a correlation of human diagnostic experience with each of the many indicators that are identified in the database of step 1. In the preferred embodiment, the database step 2 includes a low value, a high value and a mean value for each of the indicators.

Table 3 represents the database of step 2, comprising the human experience values related to each of the indicators (1–12). Thus, the range of human experience for indicator 1 reveals a low of 0.9 units, a high of 2 units and a mathematical mean of 1.45 units.

Returning to FIG. 1, step 3 of the method of the present invention is the development of test results for a specific individual. In the present invention, the individual test results are determined from testing blood, serum, urine or other bodily fluids through medical laboratory facilities. The results are correlated in a third database which includes the appropriate numerical values for each of the various indicators found in the databases of steps 1 and 2 hereabove. Table 5 is a simple test result tabulation for a specific individual as regards each of the indicators (1–12). These test results are the common output of a blood test, urine test, etc. with regard to the known indicators. For further understanding, these test results are also presented in Table 4.

TABLE 5

| | PATIENT TEST RESULTS | | | | | | | | | | | |
|---|---|---|---|---|---|---|---|---|---|---|---|---|
| INDICATOR | 1 | 2 | 3 | 4 | 5 | 6 | 7 | 8 | 9 | 10 | 11 | 12 |
| RESULT | 1.71 | 4.1 | 114 | 16.2 | 0 | 0 | .5 | 9 | 18 | 9.77 | 2.69 | 105 |

TABLE 3

| INDICATOR | LOW | HIGH | MEAN |
|---|---|---|---|
| 1 | .9 | 2 | 1.45 |
| 2 | 3.5 | 5 | 4.25 |
| 3 | 60 | 415 | 237.5 |
| 4 | 4 | 14 | 9 |
| 5 | 0 | 3 | 1.5 |
| 6 | 0 | 200 | 100 |
| 7 | .2 | 1.3 | .75 |
| 8 | 8 | 20 | 14 |
| 9 | 6 | 25 | 15.5 |
| 10 | 8.8 | 10.1 | 9.45 |
| 11 | 1.3 | 3.3 | 2.3 |
| 12 | 95 | 105 | 100 |
| . | . | . | . |
| . | . | . | . |
| . | . | . | . |

Table 4 presents a typical tabulation of some known indicators with test results to provide added understanding by way of specific example. These test results and human experience low and mean are derived from known in medical research, and step 2 thus comprises a database of known medical research.

As depicted in FIG. 1, step 4 of the method of the present invention is the computerized comparison of the individual's indicator test results from the database developed in step 3 with the human experience database for the indicators developed in step 2. The comparison of step 4 is conducted utilizing the equation:

$$\% \text{ Status} = \frac{\text{Result} - \text{Mean}}{\text{Range (High-Low)}}$$

This comparison yields a result denoted as "percent status", which is a mathematical value which expresses a comparison of the individual's test results for a specific indicator with the typical human experience test result values for that indicator. It is an indication of where the individual's test results fall in comparison with the human experience test results of Table 3. Table 6 represents the step 4 comparison of the individual test results of Table 5 with the indicator statistics of Table 3 to derive a "percent status" according to the comparison equation presented above. For further understanding, the comparison results of step 4 (% status) are also presented in Table 4.

TABLE 4

| INDICATOR | RESULT | LOW | HIGH | MEAN | % STATUS | PRESENCE LEVEL |
|---|---|---|---|---|---|---|
| 1. A/G Ratio | 1.71 | 0.9 | 2 | 1.45 | 23.48 | N |
| 2. Albumin | 4.1 | 3.5 | 5 | 4.25 | −10.00 | N |
| 3. Alkaline Phosphatase | 114 | 60 | 415 | 237.5 | −34.79 | D |
| 4. Anion Gap | 16.2 | 4 | 14 | 9 | 72.00 | I |
| 5. Basophils | 0 | 0 | 3 | 1.5 | −50.00 | D |
| 6. Basophil Count | 0 | 0 | 200 | 100 | −50.00 | D |
| 7. Bilirubin, Total | 0.5 | 0.2 | 1.3 | 0.75 | −22.73 | N |
| 8. B.U.N. | 9 | 8 | 20 | 14 | −41.67 | D |
| 9. B.U.N./Creatinine Ratio | 18.00 | 6 | 25 | 15.5 | 13.16 | N |
| 10. Calcium | 9.77 | 8.8 | 10.1 | 9.45 | 19.23 | N |
| 11. Calcium/Phosphorus Ratio | 2.69 | 1.3 | 3.3 | 2.3 | 19.72 | N |
| 12. Chloride | 105 | 95 | 105 | 100 | 50.00 | I |
| . | . | . | . | . | . | . |
| . | . | . | . | . | . | . |
| . | . | . | . | . | . | . |

TABLE 6

| INDICATOR | PRESENCE OF THE INDICATOR | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| % STATUS | 23.4 | −10 | −34 | 72 | −50 | −50 | −22 | −41 | 13 | 19 | 19 | 50 |
| PRESENCE LEVEL | N | N | D | I | D | D | N | D | N | N | N | I |

As depicted in FIG. 1, step 5 of the method of the present invention is the further analysis of the results of step 4 to determine the degree of presence of the various indicators in the specific individual's test results. In the present invention, where the percent status is greater than 25%, it is determined that an "increased level" (I) of that indicator is present. Where the percent status value of an indicator is less than −25%, it is determined that a "decreased level" (D) of that indicator is present. Where the percent status of an indicator is between −25% and +25, it is determined that a "normal level" (N) of that indicator is in the individual's test results. Table 6 includes the results of step 5, wherein an "I" represents an increased level presence, an "N" represents a normal level presence and a "D" indicates a decreased level presence of the various indicators. For further understanding, the presence indicator results of step 5 (I, N or D) are also presented in Table 4.

As depicted in FIG. 1, step 6 of the method of the present invention is the comparison of the indicator presence results of step 5 with the database of step 1. This correlation seeks to determine from the presence levels of various indicators in the individual's test results (I, N or D), the probability that particular diseases identified by the presence of specific combinations of indicators are afflicting the individual. This probability is derived by determining how many "matches" exist between the presence levels (I, N or D) of the indicator test results with the indicator data of the step 1 database.

TABLE 7

| DISEASE | DISEASE INDICATOR | | |
|---|---|---|---|
| | # INDICATORS | # MATCHES | % MATCH |
| A | 5 | 0 | 0% |
| B | 6 | 4 | 67% |
| C | 5 | 2 | 40% |
| . | . | . | . |
| . | . | . | . |
| . | . | . | . |

For instance, as depicted in Table 7, the presence levels (I, N or D) of the various indicators are compared with various diseases A, B, C . . . from the step 1 database as shown in Table 1 to determine the degree to which any of the diseases are indicated by the matching of the presence levels of various indicators with the disease data. Thus, as set forth in Table 7, it is seen that disease B is very likely present because 4 of 6 of the indicator levels are matched, whereas diseases A and C are not as likely present because fewer of the indicators levels for these diseases are matched. Table 8 is merely exemplificative of a portion of a typical result tabulation that is similar to Table 7 for added understanding.

TABLE 8

| DISEASE | ICD-9 CODE | # OF MATCHES | # OF IN-DICATORS | PERCENT MATCH |
|---|---|---|---|---|
| Anterior Pituitary Hypofunction | 253.40 | 5 | 10 | 50.00% |
| Pernicious Anemia | 281.00 | 6 | 15 | 40.00% |
| Vitamin C Deficiency | 267.00 | 3 | 8 | 37.50% |
| Rheumatoid Arthritis | 714.00 | 5 | 15 | 33.33% |
| Acute Myocardial Infarction | 410.00 | 5 | 15 | 33.33% |
| . | . | . | . | . |
| . | . | . | . | . |

Therefore, the method presented herein enables a medical practitioner to input a patient's test results into a computerized system and have the system produce a listing of possible diseases that the patient may have based upon the variation between the individual's test results and the known human experience results for various indicators.

What I claim is:

1. A medical diagnostic method utilizing a computerized system having a means for data storage and a means for data processing comprising:

storing a first database in said means for data storage, said first database having indicator data including a plurality of diseases and a plurality of indicators that are associated with each said disease;

storing a second database in said means for data storage; said second database having indicator data including human experience test result levels associated with each said indicator;

inputting test results for an individual into said means for data processing, said test results including specific indicator levels associated with said individual;

determining an indicator presence level for said indicators by comparing said specific indicator levels with said indicator data of said second database utilizing said means for data processing;

comparing said indicator presence levels with said indicator data of said first database utilizing said means for data processing to provide a determination related to the presence of particular ones of said diseases in said individual.

2. A method as described in claim 1 wherein said indicator data of said first database includes a correlation of said diseases with increased, normal and decreased levels of said indicators.

3. A method as described in claim 1 wherein said step of determining an indicator presence level includes the further step of determining whether said indicator presence level is increased, normal or decreased.

4. A method as described in claim 1 wherein said indicator data of said second database includes a correlation of high, low and mean human experience test results for said indicators.

5. A method as described in claim 4 wherein said step of determining an indicator presence level includes the further step of determining a percent status value for each said indicator, said percent status value being determined from the relationship:

$$\% \text{ Status} = \frac{\text{Test Result} - \text{Mean}}{\text{Range (High-Low)}},$$

6. A method as described in claim 5 wherein said step of determining an indicator presence level includes the further step of determining whether said percent status value is greater than 25%, less than −25% or between 25% and −25%.

7. A medical diagnostic method utilizing a computerized system having a means for data storage and a means for data processing, comprising:

storing a first database in said means for data storage, said first database having indicator data including a plurality of diseases and increased, normal or decreased levels of a plurality of indicators that are associated with each said disease;

storing a second database in said means for data storage; said second database having indicator data including human experience test result levels associated with each said indicator;

inputting test results for an individual into said means for data processing, said test results including specific indicator levels associated with said individual;

determining an increased, normal or decreased indicator presence level for said indicators by comparing said specific indicator levels with said indicator data of said second database utilizing said means for data processing;

comparing said indicator presence levels with said indicator data of said first database utilizing said means for data processing to provide determination related to the presence of particular ones of said diseases in said individual.

8. A method as described in claim 7 wherein said indicator data of said second database includes a correlation of high, low and mean human experience test results for said indicators.

9. A method as described in claim 8 wherein said an indicator presence level includes the further step of determining a percent status value for each said indicator, said percent status value being determined from the relationship:

$$\% \text{ Status} = \frac{\text{Test Result} - \text{Mean}}{\text{Range (High-Low)}},$$

10. A method as described in claim 9 wherein said step of determining an indicator presence level includes the further step of determining whether said percent status value is greater than 25%, less than −25% or between 25% and −25%.

* * * * *

UNITED STATES PATENT AND TRADEMARK OFFICE
CERTIFICATE OF CORRECTION

PATENT NO    :   5,746,204
DATED        :   May 5, 1998
INVENTOR(S): Mark A. Schauss and Patricia Kane It is certified that error appears in the above-identified patent and that said Letters Patent is hereby corrected as shown below:

On the title page: Item [75]
    Add co-inventor Patricia Kane, whose address

Millville, New Jersey, USA

Signed and Sealed this

Twentieth Day of June, 2000

*Attest:*

Q. TODD DICKINSON

*Attesting Officer*          *Director of Patents and Trademarks*